US006832393B2

(12) United States Patent
Folkesson

(10) Patent No.: US 6,832,393 B2
(45) Date of Patent: Dec. 21, 2004

(54) SAFETY VISOR

(75) Inventor: Jan Folkesson, Varnamo (SE)

(73) Assignee: Peltor AB (SE)

( * ) Notice: Subject to any disclaimer, the term of this patent is extended or adjusted under 35 U.S.C. 154(b) by 126 days.

(21) Appl. No.: 10/018,284

(22) PCT Filed: May 5, 2001

(86) PCT No.: PCT/SE00/00892

§ 371 (c)(1),
(2), (4) Date: Nov. 8, 2001

(87) PCT Pub. No.: WO00/70978

PCT Pub. Date: Nov. 30, 2000

(65) Prior Publication Data

US 2003/0097702 A1 May 29, 2003

(30) Foreign Application Priority Data

May 11, 1999 (SE) .............................................. 9901732

(51) Int. Cl.⁷ ................................................. A42B 1/06
(52) U.S. Cl. ...................... 2/410; 2/5; 2/175.1; 2/195.1
(58) Field of Search ........................... 2/9, 12, 6.3, 171, 2/195.1, 195.2, 195.3, 195.4, 195.5, 195.6, 207, 209.7, 410, 5, 175.1

(56) References Cited

U.S. PATENT DOCUMENTS

| 1,959,915 | A | | 5/1934 | Guthrie ........................... 88/41 |
|---|---|---|---|---|
| 2,874,387 | A | * | 2/1959 | Bannister et al. ............. 2/195.1 |
| 3,128,474 | A | * | 4/1964 | Feldman ...................... 2/195.6 |
| 4,292,689 | A | * | 10/1981 | Townsend, Jr. .................. 2/12 |
| 4,551,860 | A | * | 11/1985 | Smit et al. .................... 2/209.7 |
| 4,831,665 | A | * | 5/1989 | Palmaer .............................. 2/9 |
| 4,945,575 | A | * | 8/1990 | Townsend ........................ 2/12 |
| 5,159,720 | A | * | 11/1992 | Scott, Jr. ........................ 2/171 |
| 5,487,191 | A | * | 1/1996 | Ridley .......................... 2/195.1 |
| 5,640,711 | A | | 6/1997 | Lefort et al. .................... 2/6.3 |
| 5,781,933 | A | * | 7/1998 | De Giacomi ................. 2/195.1 |
| 5,933,869 | A | * | 8/1999 | Allen ............................ 2/207 |

FOREIGN PATENT DOCUMENTS

| EP | 0689812 A2 | 3/1996 | |
|---|---|---|---|
| FR | 826990 | 4/1938 | |
| SE | 454 237 | 4/1988 | |
| SE | 506057 C2 | 11/1997 | |
| WO | WO 97/30606 * | 8/1997 | ............ A42B/3/22 |

* cited by examiner

Primary Examiner—Gary L. Welch
(74) Attorney, Agent, or Firm—Cantor Colburn LLP

(57) ABSTRACT

A safety visor is produced by etching of metal and a grid that defines a large number of light-permeating holes. The safety visor has at least two zones where the holes are of different areas and/or configuration. An upper central zone has greater light transmission than the remaining zones of the safety visor. The C—C spacing for the hole is constant in both the vertical and lateral directions regardless of in which region of the safety visor the holes are located. In one preferred embodiment, the holes are hexagonal with two approximately parallel sides that are longer than the remaining sides and are directed in the vertical direction of the safety visor.

19 Claims, 2 Drawing Sheets

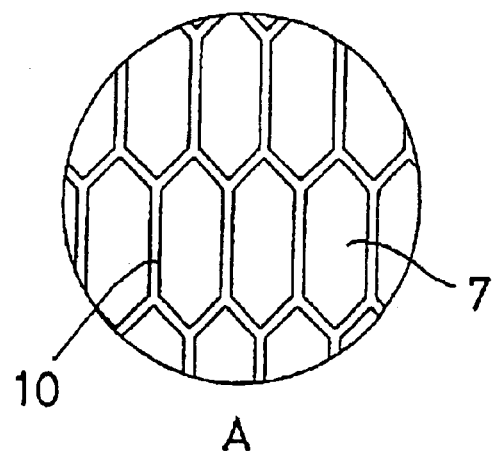
A
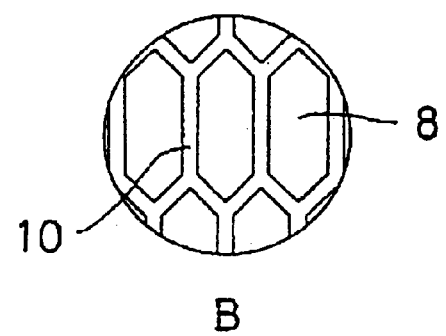
B
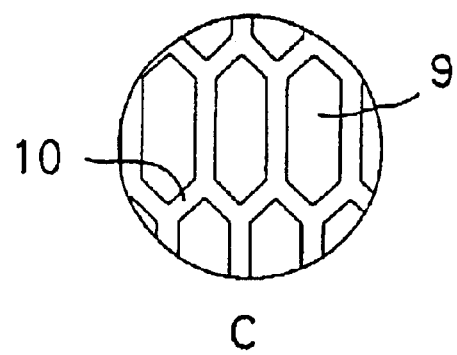
C
Fig 2

SAFETY VISOR

FIELD OF THE INVENTION

The present invention relates to a safety visor which is produced by etching of metal and which comprises a grid defining a large number of light-permeable holes.

DESCRIPTION OF THE RELATED ART

Safety visors for use primarily within forestry are previously known in numerous variations and designs.

As its name suggests, a safety visor is intended to protect the wearer's face, but above all eyes without obscuring the wearer's view to any appreciable degree. There are essentially two risk factors which the safety visor is to reduce or preferably wholly eliminate. First, the safety visor is to keep out flying matter such as dust, sawdust and the like. Secondly, the safety visor must protect against penetration by sharp objects such as small branches, twigs etc. Flying foreign matter often enters obliquely from beneath, while, on the other hand, sharp objects can come from any direction whatever.

There are previously known in the art safety visors which consist of sparsely woven metal wire. Such safety visors can provide adequate protection against flying foreign matter if the mesh is suitably small, but on the other hand, protection against penetration by pointed or sharp objects is considerably poorer, since the individual wires in the safety visor slide in relation to each other.

It is also previously known in the art to produce safety visors by the application of an etching process on sheet metal.

Regardless of whether the safety visor is etched or woven in metal, it naturally obstructs the view of the wearer more or less seriously. In order to obviate this problem, for example BP 689 812 calls for the manufacture of safety visors from two different materials with a central region of the visor formed from a transparent view plate while the peripheral parts consist of woven metal mesh.

The transparent view plate affords a good view as long as it is new, but is rapidly scratched and as a result deteriorates in quality. Further, a view plate of the type employed here often causes problems by misting over.

PROBLEM STRUCTURE

The present invention has for its object to design the safety visor intimated by way of introduction such that the drawbacks inherent in prior art technology are obviated. In particular, the present invention has for its object to realize a visor which gives maximum unobstructed view within the sectors where this is most important without, to that end, any deterioration taking place in the mechanical strength or any appreciable increase in permeability to flying objects.

SUMMARY OF THE INVENTION

The object forming the basis of the present invention will be attained if the safety visor intimated by way of introduction is characterised in that it has at least two regions where the holes are of different areas and/or configuration.

As a result of this feature, the safety visor can be given a central zone, preferably located in the middle of the visor and at its upper region, where the light transmission is greater than in the rest of the visor. Below and to the sides of this zone, the safety visor displays zones with less light transmission and, as a result, improved mechanical strength and increased protection against flying objects

BRIEF DESCRIPTION OF THE DRAWINGS

The present invention will now be described in greater detail hereinbelow, with reference to the accompanying Drawings.

In the accompanying Drawings:

FIG. 2 shows various part-magnifications A–C of different zones in the safety visor in FIG. 1.

DETAILED DESCRIPTION OF THE INVENTION

Figure 1:
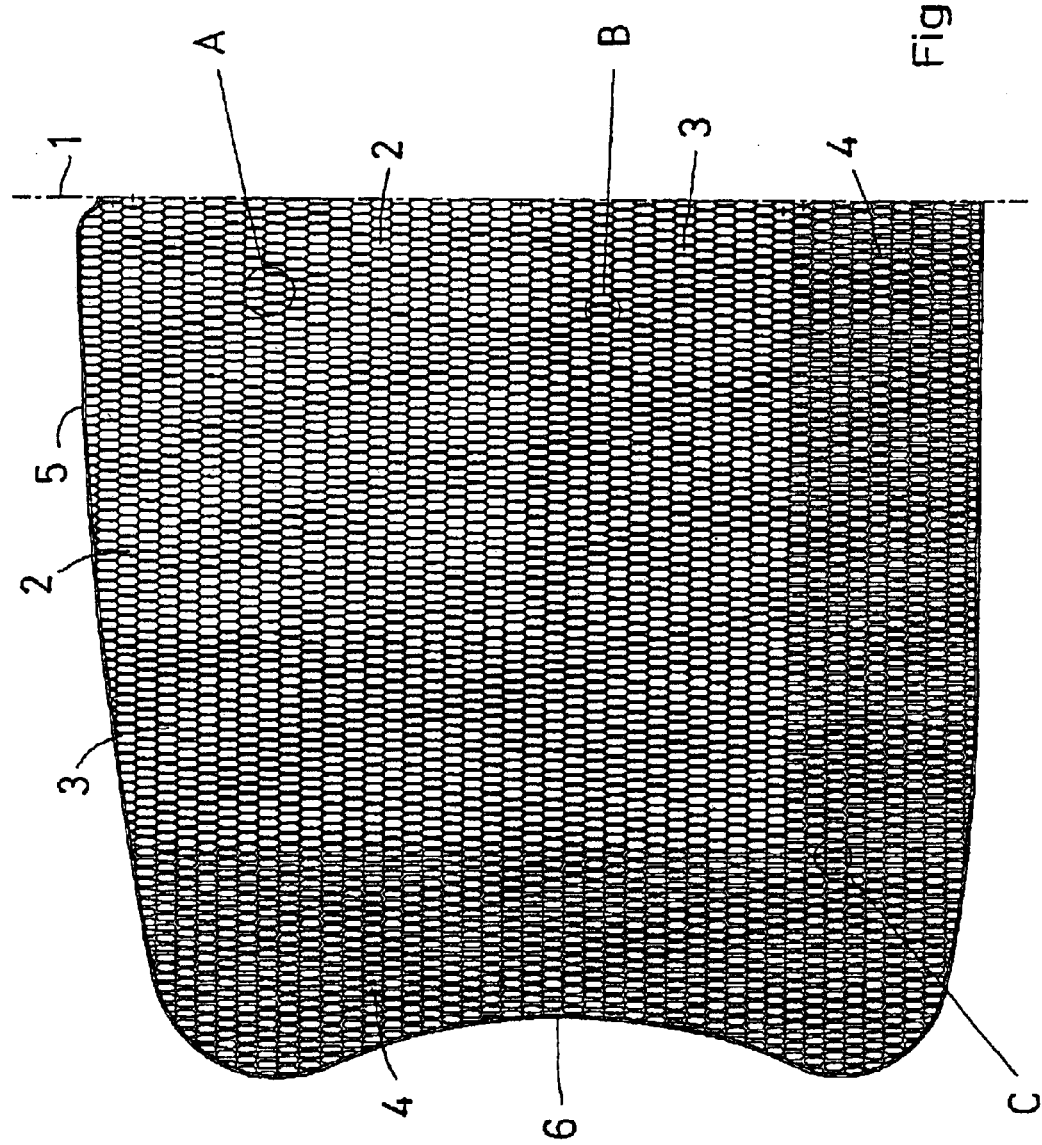
FIG. 1 shows the left-hand half of a visor designed according to the present invention.

In FIG. 1, the ghosted line 1 shows a vertical centre line of a visor according to the present invention. This implies that the illustrated part of the visor is the left-hand half of the visor and consequently that the visor has a right-hand half which is a mirror reflection of the illustrated half.

The visor is manufactured by an etching process in suitable sheet material, for example stainless steel. As a result of the etching process, certain parts of the original sheet material are removed so that a grid is left which defines or delimits a large number of light-permeating holes in the visor.

The visor is designed with an upper central zone 2 with a light permeability or light transmission capability of approx. 80%. This upper central zone extends from the upper edge 5 of the visor and downwards to approximately half of the height of the visor. In the lateral direction, it covers approximately half of the width of the visor. In the illustrated embodiment, the upper central zone is approximately rectangular in configuration, but may also have more rounded-off shape.

Below and to the sides of the upper central zone, there is an intermediate zone 3 with a light transmission capability of approx. 70%. At the centre line 1 of the visor, this intermediate zone has a height of the order of magnitude of ¼ of the total height of the visor. Further, it extends from the vertical side edges of the upper central zone approximately half way out towards the side edges 6 of the visor.

The remaining zone of the visor, i.e. its side edge regions and lower region form a lower edge zone 4 with a transmission capability for light of the order of approx. 60%.

A large light transmission capability as in the upper central zone 2 however entails that the remaining material in the grid is only 20% of the total surface. It follows from this that a region of the visor with such a high transmission capability can be mechanically weaker than that which applies to the lower edge zone with a light transmission capability of the order of 60% where the grid constitutes 40% of the original sheet material.

By placing the different zones 2, 3 and 4 of the visor in the above-described manner in relation to one another, theme will be obtained a central view area with a superior light transmission capability and lower and side areas with above all great mechanical strength and affording good protection against flying objects and penetration.

FIG. 2 shows detail magnifications of the areas A, B and C shown in FIG. 1. It will be apparent from FIG. 2 that the holes in the different zones 2, 3 and 4, respectively of the visor have the same shape but different sizes. This is achieved in that the holes 7, 8 and 9 have the same distance centre to centre in both the horizontal and vertical directions.

The result will be that the bars included in the grid which, thus, are left in place on etching of the original sheet material, are of different widths in the alternatives A, B and C.

It will further be apparent from FIG. 2 that the holes 7, 8 and 9 are all hexagonal in configuration with considerably shorter extent in the horizontal direction than in the vertical direction. As a result, the holes are tall and narrow, which has proved to afford major advantages by a reduction in reflection. This form also entails that randomly shaped particles which hit the visor with random orientation have a considerably smaller chance of passing through the holes in the same size ratio between the particles and the holes than would be the case if the holes had had the same lateral extent as vertical extent while retaining surface area, i.e. the same degree of transmission.

In part figure A in FIG. 2, in the illustrated embodiment the hole 7 has a total vertical extent of 4.0 mm and a total width of 1.5 mm. The corresponding values for FIG. B are 3.82 mm and 1.38 mm. In alternative C, the height is 3.65 mm while the width is 1.25 mm. The width of the grid bars 10 defining the holes is, in alternative A 0.25 mm, in alternative B 0.38 mm and in alternative C 0.5 mm.

The above-described design and construction of the grid and the holes 7, 8 and 9 lacks irregularities in the grid, for which reason it need not be feared that the grid zones with different transmission capabilities do not "fit together" in the interface area. Further, the above-described construction entails that the borderline between the zones of different transmission capabilities may be formed in principle in any optional manner.

What is claimed is:

1. A safety visor for protecting a wearer's face from airborne matter, such as sawdust, and from being hit by sharp objects, such as branches, the visor comprising:
   a grid made from sheet material; and
   a plurality of light permeating holes in the grid, the plurality of holes including a first group of holes having a first area and provided together within a first zone of the grid and a second group of holes having a second area and provided together within a second zone of the grid, said first zone being provided in front of the wearer's eyes, and said second area is different from said first area.

2. The visor of claim 1, wherein the first zone is an upper central zone and the second zone is located below the first zone.

3. The visor of claim 1, further comprising an upper central zone, an intermediate zone located around the upper central zone and a lower edge zone located around the intermediate zone; wherein a light transmission in the upper central zone is greater than in the intermediate zone, and a light transmission in the intermediate zone is greater than in the edge zone.

4. The visor of claim 1, wherein the first group of holes and the second group of holes have a same C—C spacing in a lateral direction.

5. The visor of claim 1, wherein the first group of holes and the second group of holes have a same C—C spacing in a vertical direction.

6. A safety visor for protecting a wearer's face from airborne matter, such as sawdust, and from being hit by sharp objects, such as branches, the visor comprising;
   a grid made from sheet material; and
   a plurality of light permeating holes in the grid, the plurality of holes including a first group of holes having a first area and providing together within a first zone of the grid and a second group of holes having a second area and provided together within a second zone of the grid, said second area is different from said first area,
   wherein a first bridge separating two adjacent holes in the first group have a first width and a second bridge separating two adjacent holes in the second group have a second width, the first width being smaller than the second width.

7. A safety visor for protecting a wearer's face from airborne sawdust and small tree branches, the visor comprising:
   a grid made from sheet material; and
   a plurality of light permeating holes in the grid, the plurality of light permeating holes includes a first group of holes having a first light transmission and a second group of holes having a second light transmission,
   wherein the first group of holes are disposed in an upper central zone of the grid and the second group of holes are disposed in a second zone, the second zone said first zone being provided in front of the wearer's eyes, and is located below the first zone, and the second light transmission is less than the first light transmission.

8. The visor of claim 7, wherein the first group of holes all having a first area and the second group of holes all having a second area, the first area being larger than the second area.

9. The visor of claim 7, further comprising a lower edge zone located around the second zone and the lower edge zone has a third light transmission, wherein the second light transmission is greater than the third light transmission.

10. The visor of claim 7, wherein the first group of holes and the second group of holes have a same C—C spacing in a lateral direction regardless of a location of the holes.

11. The visor of claim 7, wherein the first group of holes and the second group of holes have a same C—C spacing in a vertical direction.

12. A safely visor for protecting the wearer's face from airborne matter and injury, the visor comprising:
   a grid made from sheet material; and
   a plurality of light permeating holes in the grid, the plurality of holes having a first group of holes all having a first area and provided together within a first zone of the grid, the first zone being provided in front of the wearer's eyes, and the plurality of holes having at least a second group of holes all having a second area smaller than the first area and provided together within a second zone of the grid, said second zone being located below the first zone.

13. The visor of claim 12, further comprising a third group of holes all having a third area that is smaller than the second area and provided together in the third zone of the grid, the third zone being located around the second zone.

14. The visor of claim 12, wherein the first group of holes and the second group of holes have a same C—C spacing in a lateral direction.

15. The visor of claim 12, wherein the first group of holes and the second group of holes have a same C—C spacing in a vertical direction.

16. A safety visor for protecting a wearer's face from airborne matter, such as sawdust, and from being hit by sharp objects, such as branches, the visor comprising:
   a grid made from metal sheet material; and
   a plurally of light permeating holes in the grid, the plurality of holes having at least a first area and a second area smaller than the first area, the plurality of holes having the first area being located together in front of the wearer's eyes.

17. The safety visor of claim 16, wherein the plurality of holes having the second area being located together and below the plurality of holes having the first area.

18. A safety visor for protecting a wearer's face from airborne matter, such as sawdust, and from being hit by sharp objects, such as branches, the visor comprising:

a grid made from metal sheet material; and a plurality of light permeating holes in the grid, the plurality of holes having at least a first area and a second smaller area, all of the holes having generally a same shape and having a shorter extent in a horizontal direction than in a vertical direction, wherein the plurality of holes having the first area being provided together and the plurality of holes having the second area being provided together and located in front of the wearer's eyes.

19. The visor of claim 18, wherein the first area is larger than the second area.

* * * * *